United States Patent [19]
Witlin et al.

[11] Patent Number: 5,718,227
[45] Date of Patent: Feb. 17, 1998

[54] SOUND LOCALIZATION USING PARAMETRIC ULTRASOUND

[75] Inventors: Michael N. Witlin, Reston; Kenneth Richard Knowles, Manassas, both of Va.

[73] Assignee: Lockheed Martin Corporation, Bethesda, Md.

[21] Appl. No.: 510,276

[22] Filed: Aug. 2, 1995

[51] Int. Cl.⁶ .................................................. A61B 8/00
[52] U.S. Cl. ........................... 128/660.02; 128/773
[58] Field of Search ........................... 128/653.1, 660.01, 128/660.02, 661.02, 661.03, 661.04, 661.07, 662.04, 715, 773

[56] References Cited

U.S. PATENT DOCUMENTS

| | | | |
|---|---|---|---|
| 3,483,860 | 12/1969 | Namerow | 128/653.1 |
| 3,577,981 | 5/1971 | Kuris | 128/661.07 |
| 3,982,528 | 9/1976 | Phillips | 128/661.01 |
| 4,052,977 | 10/1977 | Kay | 128/661.07 |
| 4,292,678 | 9/1981 | Kay | 367/102 |
| 4,819,649 | 4/1989 | Rogers et al. | 128/660.02 |
| 5,088,498 | 2/1992 | Beach et al. | 128/661.07 |
| 5,255,685 | 10/1993 | Parra | 128/773 X |

*Primary Examiner*—Francis Jaworski
*Attorney, Agent, or Firm*—Lane, Aitken and McCann

[57] ABSTRACT

A transmitter directs a narrow RF ultrasonic beam through a body cavity to a receiver on the other side of the cavity. The beam is steered to be intercepted by audio signal sources in the body cavity, such as a fetal heart or multiple fetal hearts, which modulate the ultrasonic beam. The received parametric beam is demodulated and filtered to provide a relatively noise free audio reproduction of an audio signal source. In one embodiment, two transmitters are steered independently to direct respective beams to respective receivers to produce two signals and, thus, a binaural audio reproduction of an audio signal source. The audio reproduction is at a maximum when the two beams intersect at the audio signal source.

13 Claims, 5 Drawing Sheets

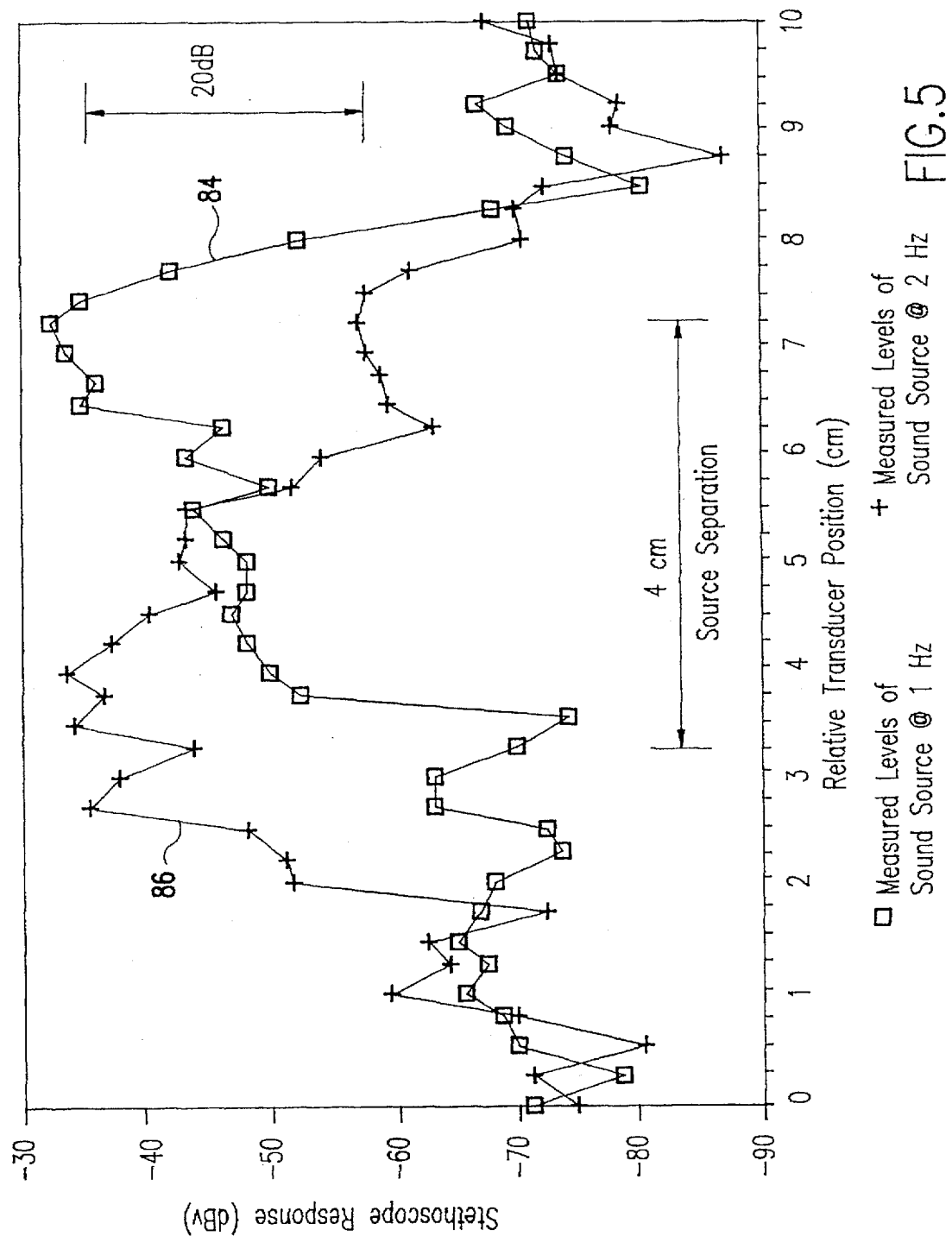

SOUND LOCALIZATION USING PARAMETRIC ULTRASOUND

BACKGROUND OF THE INVENTION

The present invention relates to an apparatus and method for sound localization using parametric ultrasound and, more particularly, to such an apparatus suitable for use as a highly directional stethoscope and a related method.

Known medical ultrasound imaging equipment provides high resolution views of anatomical cross-sections. Many physicians, however, still rely on aural clues from stethoscopes for medical diagnoses of problems not apparent on ultrasound images. Typical stethoscopes have an omnidirectional wide beam. Diagnosis with common passive stethoscopes, even those electronically enhanced, cannot provide high directivity within a body cavity and must rely on large spatial separation between sound sources and on the nature of sounds to resolve noise from more than one internal source. One area of particular interest involves discerning the heartbeat of a fetus from the heartbeat of the mother. With a typical stethoscope, doctors hear both hearts and rely on other characteristics of a fetal heart, such as its higher heart rate, to distinguish it from the mother's heart.

Known medical ultrasound devices employ pulsed RF ultrasound echolocation signals usually used for imaging, and synthesize the aural presentation from the envelope of the detected pulses being reflected back to the receiver. Standard medical ultrasound sources produce an extremely fine "pencil" beam. Only the sounds intercepting the path of this beam will modulate it. In contrast, a typical passive stethoscope, even one which has electronic amplifiers, is nearly omnidirectional and cannot isolate sounds within a body or chest cavity.

SUMMARY OF THE INVENTION

By the present invention, sound sources in any medium that supports sound transmission at RF frequencies can be located, and sounds emanating from the different sources can be resolved. In one application, the apparatus and method of the present invention can be used as a diagnostic aid to a physician, like a stethoscope but highly directional in that it will pick up only sounds intercepted by a narrow beam. When the present invention is used to listen to a fetal heart, a user can clearly hear the fetal heart, while the sound of the mother's heart is so faint as to be difficult to hear, if it can be heard at all. Conversely, the present invention can also provide the sound of the mother's heart, while the heart of the fetus is difficult to hear. In the case of multiple fetuses, the fetal hearts can be heard one at a time. The apparatus and method according to the present invention provide the user with high fidelity sound with a high degree of sound isolation. The apparatus and method may be used in conjunction with imaging equipment to provide the user with visual clues to the locations of the sound sources.

In order to achieve the above advantages, one or two continuous low-frequency RF ultrasound sources are used, each to create a narrow beam which is passed through a sound transmission medium to an associated ultrasound receiver. Audible low frequency sound sources within the medium phase-modulate the ultrasound beam when the beam intercepts the sound sources after the fashion of a parametric amplifier. Each receiver is a transducer at which the parametric signal defined by the associated ultrasound beam is demodulated, filtered and amplified to provide the listener with a high fidelity representation of the internal sound along the RF ultrasound beam path. Each transmitter is also a transducer having an aperture with a typical dimension of tens of wavelengths of the RF frequency used for the beam. Such transmitters produce very narrow beams. Each narrow beam is modulated only by the sound sources which intercept it. Any interfering sounds not within the narrow beam, which would be heard by an ordinary stethoscope, are suppressed by the present invention so that they are heard barely, if at all. Thus, two internal and audible sound sources spatially separated can be aurally distinguished one at a time.

When two transmitters and receivers are used, the parametric beams of the apparatus and method of the present invention provide very precise localization as well as discrimination, because the transmitters are spaced from one another and the beams are steered to pass through at a single sound source of interest. Each beam provides a separate signal, one for each ear. The perceived signal strength peaks when a sound source within the medium is located at the intersection of the beams. That is, the two beams, steered independently, provide the binaural capability, one demodulated beam per ear, and the perceived strength of the signal of each of the two RF ultrasound beams is reinforced when each of the parametric beams is intercepted by the same internal sound source, thus localizing the source within the medium, for example, a three-dimensional cavity. The perception is that the strength of the signals is more than double the sound of one beam intercepting the internal sound source: the strength is perceived to be about four times the strength of the signal coming from one beam.

The RF ultrasound beam is continuous and tomographic because the receiver of the RF ultrasound is in opposition to the source. Continuous demodulation of each RF beam recovers the original internal sound intercepted by that beam. Each RF beam can be steered independently. Binaural listening reinforces any sound source located at the intersection of the RF beams, further enhancing the resolution of the listening technique.

BRIEF DESCRIPTION OF THE DRAWINGS

FIG. 5 is a graph showing the measured sound output level as a function of the horizontal displacement of the system according to the present invention relative to internal sound sources in the experimental set up of FIG. 3.

DETAILED DESCRIPTION OF THE PREFERRED EMBODIMENTS

Figure 1:
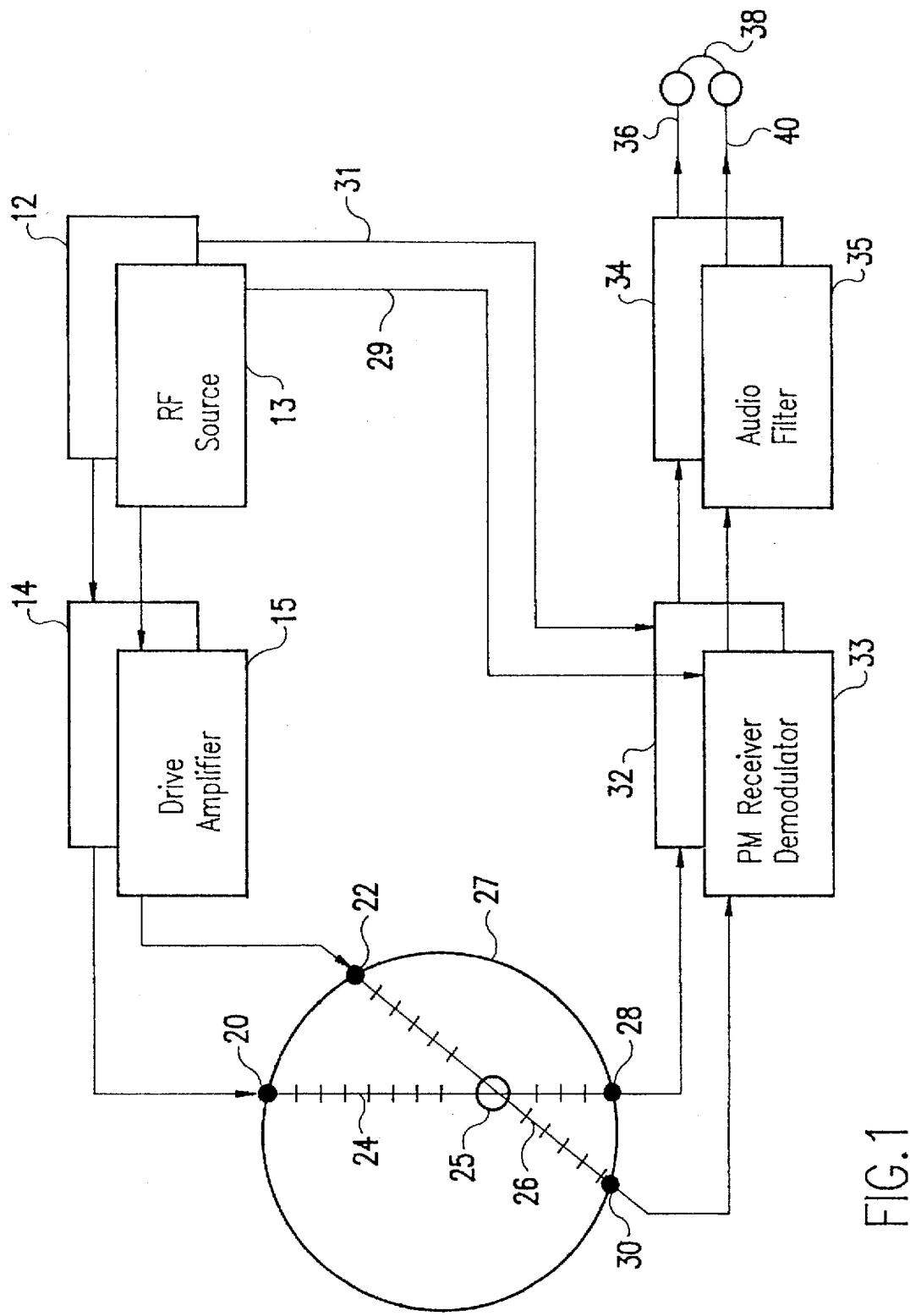
FIG. 1 is a schematic diagram for a binaural sound localization system according to the present invention.

A binaural embodiment of the present invention, which localizes, recognizes and discriminates internal sound sources, is shown in FIG. 1. Two independent and continuous RF sources 12, 13 and drive amplifiers 14, 15 feed signals to a pair of transmitting transducers 20 and 22 to produce ultrasound beams 24 and 26, respectively, directed into an object 27 having an internal sound source 25, such as a human body with its heart as an internal sound source. It is preferred that the RF sources 12, 13 be independent and produce different frequencies from one another. The beams 24 and 26 may be steered by the user independently of one another, mechanically and/or electronically, to sweep through the object 27 to find the internal sound source 25. Each of a pair of RF ultrasound receiving transducers 28 and 30 positioned on an opposite side of the object 27 from the transmitting transducers 20 and 22, respectively, produces an electrical signal representing the modulated RF ultrasound.

The steering can be done mechanically by providing a mechanical arrangement to move each transmitting transducer and its associated receiving transducer around the perimeter of the object 27, with the transmitting and receiving transducers always facing each other. The steering can be done electronically by, for example, providing a multitude of transmitting transducers and associated receiving transducers in a one-dimensional or two-dimensional pattern around the periphery of the object 27 and stepping the beam through the multitude until the best beam passing through the internal sound source 25 is identified by listening. Each transmitting transducer and each receiving transducer can comprise either a single cell or a one-dimensional or two-dimensional array of cells. If transmitting and/or receiving transducers are themselves arrays of cells, then vernier steering implemented by electronically delaying the signals appropriately from cell to cell within the transducer can be used to improve the localization capability. The receiving transducers can be interspersed among the transmitting transducers in an alternating pattern. Where the multitude of transmitting transducers and associated receiving transducers described are used, the transmitting transducers 20, 22 and the receiving transducers 28, 30 shown in FIG. 1 are representative of many pairs which are employed to steer beams into a sound source. Whether the steering is done electronically, mechanically, or by a combination of the two steering methods, the receiving transducer and the transmitting transducer are kept facing each other in order that the receiving transducer receives the beam.

The beams 24 and 26 are tomographic because the receiving transducers 28 and 30 are positioned opposite the transmitting transducers 20 and 22. In response to receiving the beams, the receiving transducers 28 and 30 send signals to a pair of PM (phase modulation) receiver/demodulators 32, 33. The PM receiver/demodulators 32, 33 also receive reference signals 29 and 31 from the RF sources 12, 13 and extract from the signals of the receiving transducers 28 and 30 the exact internal sounds along the tomographic beams. A pair of audio filters and amplifiers 34, 35 receives the extracted signals from the PM receiver/demodulators 32, 33 and drives a binaural, that is, stereophonic, headset 38 with left and right ear signals 36 and 40, which are derived respectively from the signals from the receiving transducers 28 and 30.

The ultrasound beams 24 and 26 can be steered independently just by listening or with the aid of ultrasound imaging equipment capable of superimposing the parametric paths on the ultrasound image scan concurrently with listening. A simple visual presentation of the sound, for example, the signals from the receiving transmitters after demodulation by the PM receiver/demodulators 32 and 33, can be sent in a conventional manner to a two-dimensional sector display on a cathode ray tube or passive cell LCD oscilloscope with a cursor provided on the screen. The use of a parametric modulation technique ensures that only sound intercepting the narrow beams 24 and 26 will be extracted, not sound anywhere else within the medium.

Figure 2:
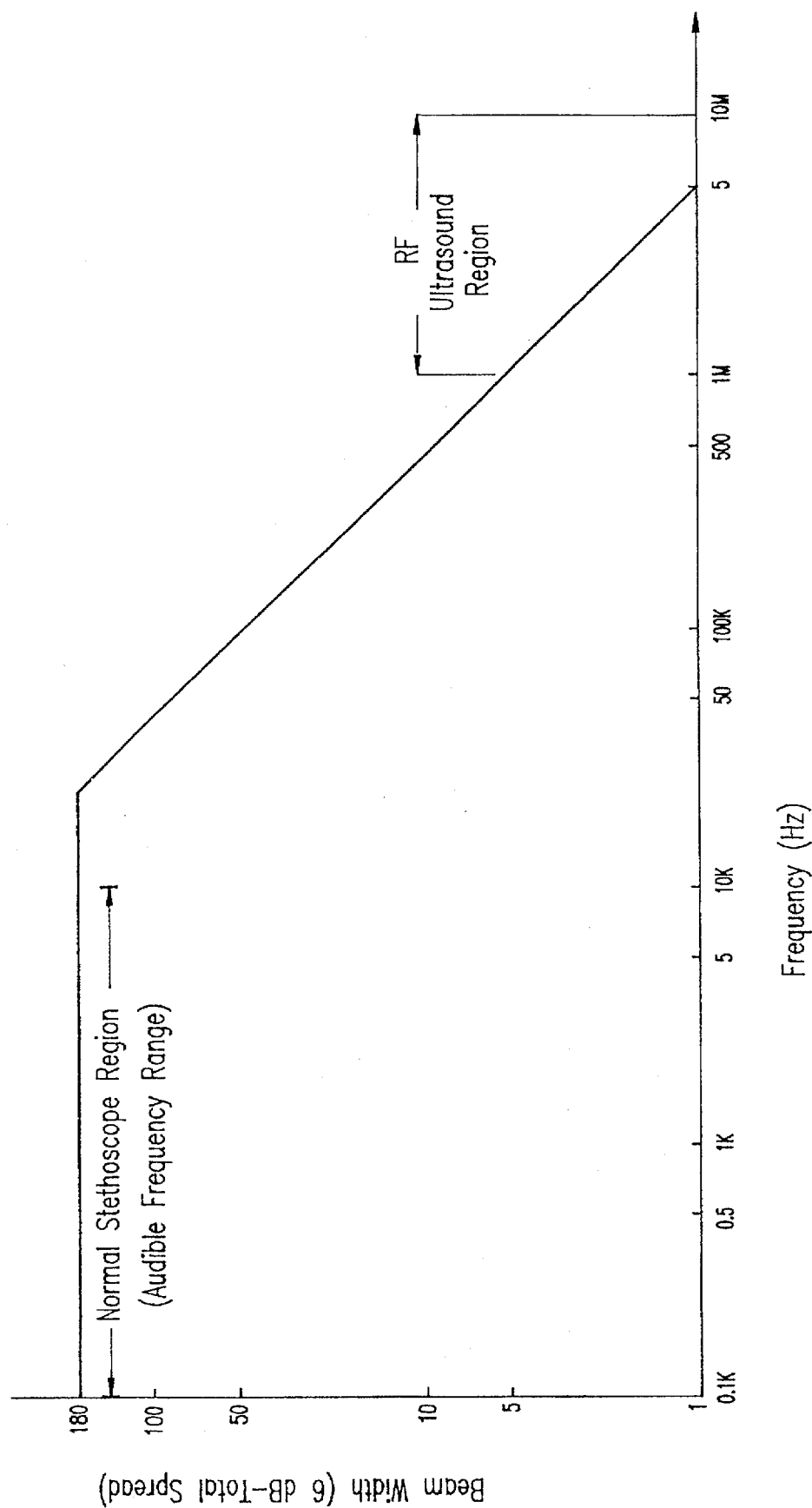
FIG. 2 is a graph showing the beam widths used for localization of internal sounds, both for the present invention and for a conventional stethoscope.

As can be seen from FIG. 2, for a beam carrying RF ultrasound above about 30 KHz and a transmitting transducer with a transmitting aperture having a diameter of 2.5 cm, significant directivity improvement, that is, beamwidth reduction, is achieved with the present invention relative to a conventional stethoscope. At 2 MHz, the width of each beam 24 and 26 of the system according to the experimental embodiment of this invention is less than 2.5 degrees, 1.25 degrees on each side of the centerline of the beam, which is more than seventy times narrower than the corresponding beam of a conventional stethoscope. A normal stethoscope with an aperture of 2.5 cm is essentially omnidirectional and cannot localize sound sources. Sounds at the edges of the beam are attenuated 6 dB from sounds at the centerline of the beam. Thus, there is a clear difference to the listener between sounds intercepted by the center of the beam and sounds intercepted by the edges of the beam. Signals beyond the edges of the beam are attenuated at least 99%. Sounds outside the beam further than 4 degrees spread from the centerline of the beam are theoretically attenuated by at least 18 dB. The greatly reduced width of the beams 24 and 26 not only localizes a sound source, but discriminates against other, interfering sources lying outside the narrow beam. An experimental measurement was made to verify this performance. Potentially interfering sounds 4 degrees or more from the centerline of the beam are not heard at all. In actual practice, it is contemplated using beams of different frequencies, for example, one beam comprising a 2 MHz signal and the other beam comprising a 1 MHz signal. The 2 MHz beam has half the width of the 1 MHz beam.

Figure 3:
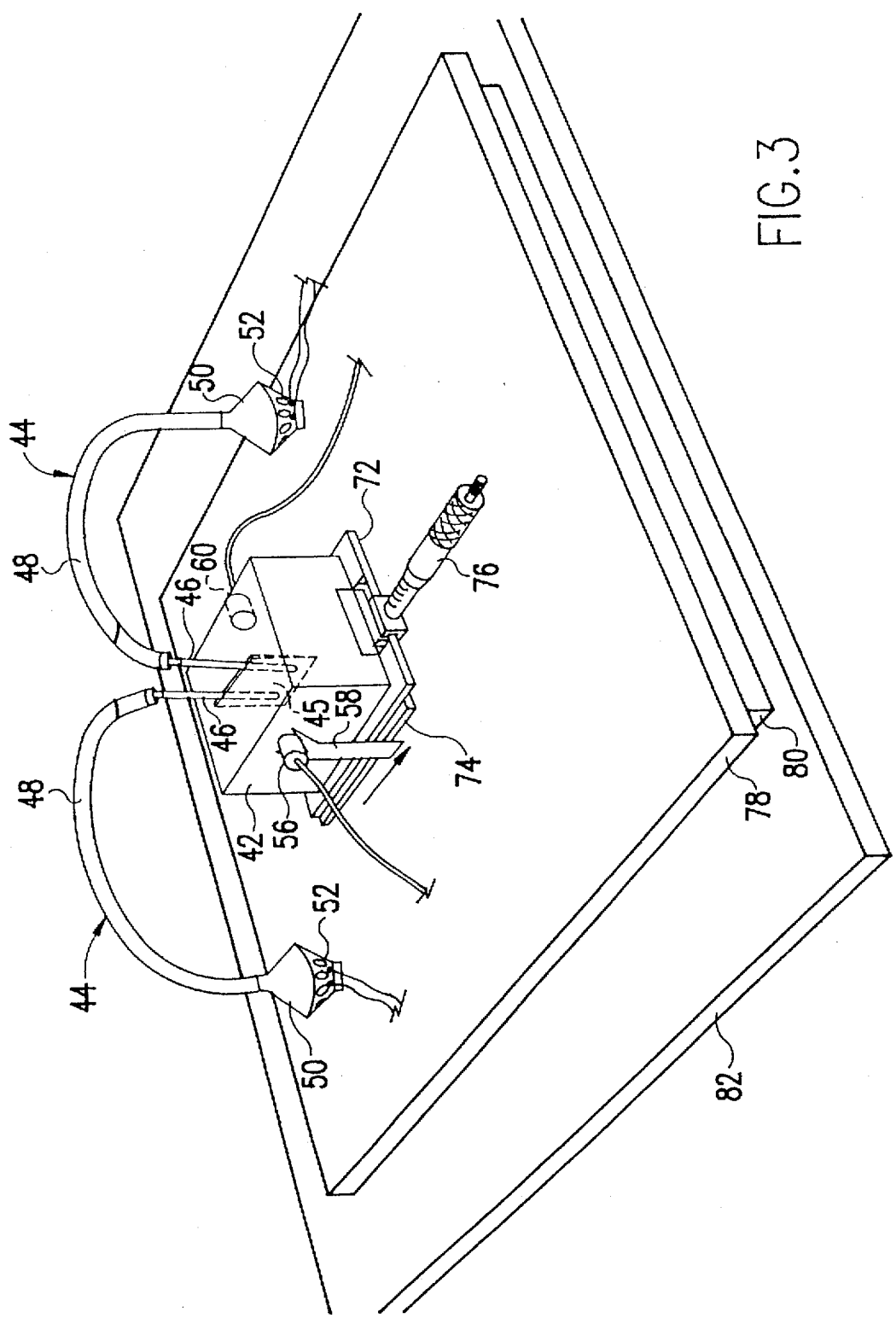
FIG. 3 is a pictorial illustration of an experimental monaural set up of the present invention with only one beam used.
Figure 4:
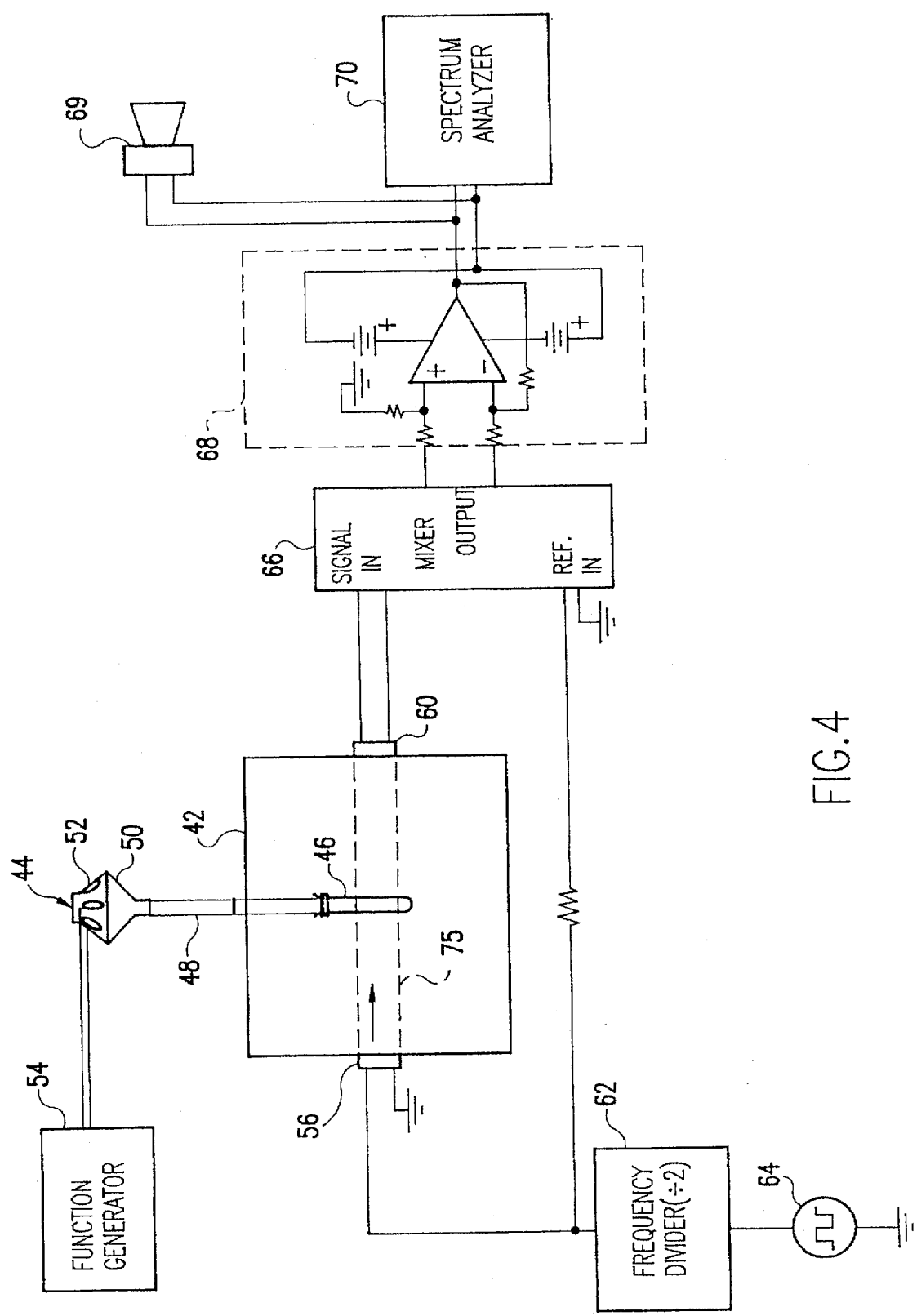
FIG. 4 is a block diagram of the experimental set up of FIG. 3.

As can be seen from FIGS. 3 and 4, in an experimental setup, a tissue simulator, or tissue phantom, 42 contains devices 44 for producing sound at two locations within the tissue simulator. The tissue simulator 42 is a commercially available device comprising a wetted mass of soft plastic having acoustic properties similar to human tissue. A slit is made in the top of the tissue simulator 42 to form a cavity 45 in the tissue simulator, and the sound-producing devices 44 are placed in the cavity at locations spaced from one another. Then, the cavity 45 is filled with water.

Each sound-producing device 44 includes a balloon 46 positioned in the cavity 45 and a tube 48 connecting the balloon to a funnel 50, which is secured by adhesive to the face of a loudspeaker 52, which can be an ordinary loudspeaker. Each loudspeaker 52 provides internal sound to its associated balloon 46 in the cavity 45. Each balloon 46 is filled with water, and the sound produced by the loudspeaker is transmitted through the air in tube 48 and the water in part of the tube 48 to the water in balloon 46. The internal sound sources in the tissue simulator 42 are the vibrating water-filled balloons 46.

The loudspeakers 52 are connected to a function generator 54, such as a Hewlett-Packard HP3310B function generator, which provides a continuous low frequency sinusoidal signal. A transmitting transducer 56 is mounted on a support 58 positioned at one side of the tissue simulator 42, and a receiving transducer 60 is mounted on a support (not shown) similar to the support 58 and positioned at the opposite side of the tissue simulator, in alignment with the transmitting transducer. Both transducers 56 and 60 can be 2 MHz ultrasonic transducers available under the part numbers 9309-3553 and 9309-3554 from Blatek, Inc. of State College, Pa., 16801. A beam emitted by the transmitting transducer 56 is directed toward the receiving transducer 60. The transmitting transducer 56 is connected to an RF frequency source, which can comprise a frequency divider 62 and a 4 MHz crystal oscillator module 64, such as a Vectron C0238-8 producing a 2 MHz RF waveform source. A signal from the receiving transducer 60 defines an input for a mixer 66, such as a Hewlett-Packard HP10514A mixer. The reference input for the mixer 66 is provided by the same RF source 62. The output from the mixer 66 is filtered and amplified in a low-noise differential amplifier circuit 68, and the output of the circuit is sent to a loudspeaker 69 and can be sent to a spectrum analyzer 70, such as a Hewlett-Packard HP3582A spectrum analyzer. The spectrum analyzer 70 measures audible output signal levels of multiple sinusoidal signals at different frequencies simultaneously. For the experimental setup, the spectrum analyzer 70 serves to measure the levels of the two internal sound sources at each beam position. The spectrum analyzer is not required as a part of the invention.

The tissue simulator 42 is mounted on a plate 72 mounted on a single-axis machine slide 74. A micrometer adjuster 76 is connected to the slide 74 for moving the plate 72 by a precise measured amount along the machine slide 74 in a direction transverse to a beam 75 transmitted by the transmitting transducer 56. The tissue simulator 42 and the balloons 46 emitting the internal sounds move relative to the transmitting and receiving transducers 56 and 60, respectively, since the transducers are mounted on the stationary supports 58. The supports 58 and the machine slide 74 are mounted on an optical table 78 resting on a sheet 80 of foam rubber on a laboratory bench 82. In a practical implementation, the stethoscope apparatus of the present invention on a supporting frame would be moved, or at least the beam would be moved, with respect to the object containing the sources.

For the experimental setup, one of the sound-producing devices 44 produces a 1 Hz internal sound and the other sound-producing device 44 produces a 2 Hz internal sound. FIG. 5 shows the response of the apparatus according to the present invention to the two internal sound sources. The balloons 44 and the tissue simulator 46 are moved in a direction transverse to the direction of the beam 75, and the positions of the balloons 44 relative to the position of the beam are shown on the horizontal axis of FIG. 5. The response of the apparatus in dBV is shown on the vertical axis. The result for the 1 Hz internal sound source is represented by the line 84 and the response for the 2 Hz sound source is represented by the line 86. It can be seen from the peak of each line at what point of the relative position of the sound source and beam that the response is a maximum. The peaks are the points where the beam passes through each internal sound source, that is, through each balloon 46. Thus, the position of each internal sound source is indicated by the position of the associated peak. It can be seen that, at the peak of each sound source, there is about a 20 dB difference between its signal level and the level of the other sound source. Thus, there is a clearly detectable difference between the sound source which intercepts the beam 75 and any nearby sound sources. More specifically, one source is suppressed by a factor of 100 (20 dB) with respect to another, which means that the suppressed source can barely be heard.

The sound heard by the user is the greatest when the beam position is at the peaks of sound levels shown in FIG. 5. Note that FIG. 5 shows that, at the peak levels of one source, the other source level is 20 dB lower even though the sources are separated by only a few centimeters. For a binaural setup, a peak can be detected at each ear of the user, and the peaks in sound occur simultaneously at both ears when both beams, such as the beams 24 and 26 of FIG. 1, are intercepted by the same internal sound source. The sound beams 24 and 26 intersect one another in these circumstances. Each beam should be at a different RF frequency separated by at least 10 KHz to prevent audible artifacts from RF beam cross modulation. Separation of RF source frequencies by a factor of two provides a low frequency wider initial search beam for one ear while the higher frequency provides finer localization beam, a factor of two narrower, for the other ear of the listener.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. An ultrasound method for locating a sound source in a body, the sound source producing a sound, comprising the steps of:

directing through the body from a transmitting transducer on one side of the body to a receiving transducer on an opposite side of the body a narrow ultrasonic beam that is modulated by the sound source, the sound being produced independent of the narrow ultrasonic beam;

sweeping the narrow ultrasonic beam through the body to direct the beam through the sound source; and demodulating and filtering said narrow ultrasonic beam to generate an audio signal that replicates the sound produced by the sound source in the body.

2. The ultrasound method of claim 1, wherein the ultrasonic beam has a centerline and a total spread about the centerline of less than 2.5°.

3. The ultrasound method of claim 1, wherein the narrow ultrasonic beam is directed through a human body.

4. The ultrasound method of claim 1, wherein two narrow and independent ultrasonic beams are directed through the body from respective transmitting transducers at first and second positions on the body to associated receiving transducers at third and fourth positions on the body opposite, respectively, from said first and second positions;

said beams are steered to direct the beams through the sound source; and the beams are demodulated and filtered separately to generate from each said beam an audio signal that replicates the sound source in the body.

5. The ultrasound method of claim 4, wherein said beams are steered independently of one another.

6. The ultrasound method of claim 4, wherein each of said audio signals is transmitted to a respective one of the ears of a person employing the method.

7. The ultrasound method of claim 5, wherein each of said audio signals is transmitted to a respective one of the ears of a person employing the method.

8. An ultrasound system for locating a sound source in a body, the sound source producing a sound, comprising in combination:

means for directing through the body a narrow ultrasonic beam that is modulated by the sound source, the sound being produced independent of the narrow ultrasonic beam;

means for receiving, demodulating and filtering said narrow ultrasonic beam to generate an audio signal that replicates the sound source in the body; and means for sweeping the narrow ultrasonic beam through the body to direct the beam through the sound source.

9. The ultrasound system of claim 8, wherein said directing means comprises a continuous RF waveform source, a drive amplifier and a transmitting transducer, and said means for receiving, demodulating and filtering comprises a receiving transducer, a demodulator and a filter.

10. The ultrasound system of claim 8, wherein said means for directing comprises means for directing two narrow ultrasonic beams through the body, including two RF frequency sources, and two transmitting transducers for positioning at first spaced positions on the body, said means for receiving, demodulating and filtering comprises means for generating from each said beam an audio signal that replicates the sound source in the body.

11. The ultrasound system of claim 10, further comprising means for steering the narrow ultrasonic beams independently of one another to direct the beams through the sound source.

12. The ultrasound system of claim 10, wherein said generating means comprises means for transmitting each of said audio signals to a respective one of the ears of a person employing the system.

13. The ultrasound system of claim 8, wherein said directing means comprises means for transmitting an ultrasonic beam having a centerline and a total spread about the centerline of less than 2.5°, with at least 99% attenuation of signals outside said spread.

* * * * *